United States Patent [19]

Gregg et al.

[11] Patent Number: 5,264,105
[45] Date of Patent: Nov. 23, 1993

[54] ENZYME ELECTRODES

[76] Inventors: Brian A. Gregg, 13940 Braun Dr., Golden, Colo. 80401; Adam Heller, 5317 Valburn Cir., Austin, Tex. 78731; Wolfgang Kerner, Universitat zu Lubeck, Klinik fur Innerere Medizin, Razeburger Allee 160, D-2400 Lubeck 1, Fed. Rep. of Germany; Michael V. Pishko, 1905 Pasadena, Austin, Tex. 78757; Ioanis Katakis, 8331 Fredericksburg, #1109, San Antonio, Tex. 78229

[21] Appl. No.: 32,806

[22] Filed: Mar. 17, 1993

Related U.S. Application Data

[60] Division of Ser. No. 880,760, May 8, 1992, which is a continuation-in-part of Ser. No. 389,226, Aug. 2, 1989.

[51] Int. Cl.$^5$ .......................................... G01N 27/26
[52] U.S. Cl. .................................. 204/403; 204/418; 435/817; 435/288
[58] Field of Search .................. 204/403, 418, 153.12; 435/817, 288

[56] References Cited

U.S. PATENT DOCUMENTS

| | | | |
|---|---|---|---|
| 4,098,574 | 7/1978 | Dappen | 435/14 |
| 4,168,205 | 9/1979 | Danninger et al. | 435/25 |
| 4,224,125 | 9/1980 | Nakamura et al. | 435/817 |
| 4,247,297 | 1/1981 | Berti et al. | 435/24 |
| 4,356,074 | 10/1982 | Johnson | 435/190 |
| 4,375,399 | 3/1983 | Havas et al. | 435/14 |
| 4,390,621 | 6/1983 | Bauer | 435/14 |
| 4,404,066 | 9/1983 | Johnson | 435/817 |
| 4,418,148 | 11/1983 | Oberhardt | 435/14 |
| 4,427,770 | 1/1984 | Chen et al. | 435/14 |
| 4,461,691 | 7/1984 | Frank | 204/290 R |
| 4,476,003 | 10/1984 | Frank et al. | 204/290 R |
| 4,524,114 | 6/1985 | Samuels et al. | 204/294 |
| 4,545,382 | 10/1985 | Higgins et al. | 204/403 |
| 4,552,840 | 11/1985 | Riffer | 435/28 |
| 4,619,754 | 10/1986 | Niki et al. | 204/290 R |
| 4,655,885 | 4/1987 | Hill et al. | 204/290 R |
| 4,711,245 | 12/1987 | Higgins et al. | 204/415 |
| 4,717,673 | 1/1988 | Wrighton et al. | 204/209 F |
| 4,721,601 | 1/1988 | Wrighton et al. | 204/435 |
| 4,758,323 | 7/1988 | Davis et al. | 435/26 |
| 4,764,416 | 8/1988 | Ueyama et al. | 428/212 |
| 4,776,944 | 10/1988 | Janata et al. | 435/817 |
| 4,784,736 | 11/1988 | Lonsdale et al. | 204/157.15 |
| 4,795,707 | 1/1989 | Niiyama et al. | 435/817 |
| 4,917,800 | 4/1990 | Lonsdale et al. | 210/490 |
| 4,927,516 | 5/1990 | Yamaguchi et al. | 435/817 |
| 4,938,860 | 7/1990 | Wogoman | 435/817 |
| 4,968,400 | 11/1990 | Shimomura et al. | 204/403 |
| 5,082,786 | 1/1992 | Nakamoto | 435/14 |

FOREIGN PATENT DOCUMENTS

| | | |
|---|---|---|
| 127958A2 | 5/1984 | European Pat. Off. |
| 0125139 | 11/1984 | European Pat. Off. |
| 0184909 | 6/1986 | European Pat. Off. |
| 0241309A3 | 4/1987 | European Pat. Off. |
| 0278647 | 8/1988 | European Pat. Off. |
| 0368209A1 | 6/1989 | European Pat. Off. |
| 0390390A1 | 3/1990 | European Pat. Off. |
| 55-012437A | 1/1980 | Japan |
| 58-049821B | 11/1983 | Japan |
| 63-309848A | 12/1988 | Japan |
| 2006737A | 1/1990 | Japan |
| 2088960A | 3/1990 | Japan |
| 2099850A | 4/1990 | Japan |
| 830229A | 5/1981 | U.S.S.R. |
| 1016306A | 5/1983 | U.S.S.R. |

OTHER PUBLICATIONS

Foulds et al., "Immobilization of Glucose Oxidase in Ferrocene-Modified Pyrrole Polymers," *Anal. Chem.*, vol. 60, No. 22, pp. 2473-2478 (1988).

(List continued on next page.)

*Primary Examiner*—John Niebling
*Assistant Examiner*—Bruce F. Bell
*Attorney, Agent, or Firm*—Pravel, Hewitt, Kimball & Krieger

[57] ABSTRACT

An improved enzyme electrode includes a three-dimensional redox polymer network having redox enzymes bound thereto, and also having a protein excluding polymeric coating.

7 Claims, 5 Drawing Sheets

OTHER PUBLICATIONS

Hale et al., "A New Class of Amperometric Biosensor Incorporating a Polymeric Electron-Transfer Mediator", *J. Am. Chem. Soc.*, vol. 111, No. 9, pp. 3482-3484 (1989).

Foulds et al., "Enzyme Entrapment in Electrically Conducting Polymers", *J. Chem. Soc., Faraday Trans. 1*, vol. 82, pp. 1259-1264 (1986).

Dengani et al., "Electrical Communication between Redox Centers of Glucose Oxidase and Electrodes via Electrostatically and Convalently Bound Redox Polymers", *J. Am. Chem. Soc.*, vol. 111, pp. 2357-2358 (1989).

Bartlett et al., "Strategies for the Development of Amperometric Enzyme Electrodes", *Biosensors*, vol. 3, pp. 359-379 (1987/1988).

Clark et al., "Electrode Systems for Continuous Monitoring in Cardiovascular Surgery", *Ann. N. Y. Acad. Sci.*, vol. 102, p. 29 (1962).

Clark et al., "Long-term Stability of Electroenzymatic Glucose Sensors Implanted in Mice", *Trans. Am. Soc. Artif. Inten. Organs*, vol. 34, pp. 259-265 (1988).

Cass et al., "Ferricinium Ion as an Electron Acceptor for Oxido-Reductases", *J. Electroanal. Chem.*, vol. 190, pp. 117-127 (1985).

Albery et al., "Amperometric enzyme electrodes", *Phil. Trans. R. Soc. Long.*, vol. B 316, pp. 107-119 (1987).

Scheller et al., "Enzyme Electrodes and their application", *Phil. Trans. R. Soc. Long*, vol. B 316, pp. 85-94 (1987).

Pollack et al., "Enzyme Immobilization by Condensation Copolymerization into Cross-Linked Polyacrylamide Gels", *J. Am. Chem. Soc.*, vol. 102, No. 20, pp. 6324-6336 (1980).

Castner et al., "Mass Transport and Reaction Kinetic Parameters Determined Electrochemically for Immobilized Glucose Oxidase", *Biochemistry*, vol. 23, No. 10, pp. 2203-2210 (1984).

Abstract of U.S. Pat. No. 4,193,982, Mar. 18, 1980, Avaremas et al.

Abstract of Brandt, et al., "Covalent attachment of proteins to polysaccharide carriers by means of benzoquinone", *Biochem. Biophys.* Acta, 386(1), 196-202 (1975).

Abstract of Narasimhan et al., "p-Benzoquinone activation of metal oxide electrodes for attachment of enzymes", *Enzyme Microb. Technol.*, 7(6), 28-6 (1985).

Abstract of Ikeda et al., "Glucase oxidase-immobilized benzoquinone-carbon paste electrode as a glucose sensor", *Agric. Biol. Chem.*, 49(2), 541-3 (1985).

Abstract of U.S. Pat. No. 4,581,336, Apr. 8, 1986, Malloy et al.

Abstract of European Patent No. 177,743 A2, Apr. 16, 1986.

Abstract of Bartlett et al., "Modification of glucose oxidase by tetrathiafulvalene", *J. Chem. Soc., Chem. Commun.*, (16), 1135-6 (1990).

Abstract of Albery et al., "Amperometric enzyme electrodes. Part II. conducting salts as electrode materials for the oxidation of glucose oxidase", *J. Electoanal. Chem. Interfacial Electrochem.*, 194(2), 223-35 (1985).

Yao, "A Chemically-Modified Enzyme Membrane Electrode as an Amperometric Glucose Sensor", *Analytica Chemica Acta*, vol. 148, pp. 27-33 (1983).

Dicks et al., "Ferrocene modified polypyrrole with immobilised glucose oxidase and its application in amperometric glucose microbiosensors", *Ann. Biol. Clin.*, vol. 47, pp. 607-619 (1983).

Yabuki et al., "Electro-conductive Enzyme Membrane", *J. Chem. Soc., Chem. Commun.*, pp. 945-946 (1989).

Trojanowicz et al., "Enzyme Entrapped Polypyrrole Modified Electrode for Flow-Injection Determination of Glucose", *Biosensors & Bioelectronics*, vol. 5, pp. 149-156 (1990).

Degani et al., "Direct Electrical Communication Between Chemically Modified Enzymes and Metal Electrodes. 1. Electron Transfer from Glucose Oxidase to Metal Electrodes via Electron Relays, Bound Covalently to the Enzyme," *Journal of Physical Chemistry*, vol. 91, pp. 1285-1289 (1987).

Degani et al., "Direct Electrical Communication Between Chemically Modified Enzymes and Metal Electrodes. 2. Methods for Bonding Electron-Transfer Relay to Glucose Oxidase and D-Amino-Acid Oxide," *JACS*, vol. 110, pp. 2615-2620 (1988).

Bartlett et al., "Covalent Binding of Electron Relays to (List continued on next page.)

OTHER PUBLICATIONS

Glucose Oxidase," *J. Chem. Soc.*, Chem. Commun., pp. 1692–1704.

Umana, U.S. Army Research Office Report No. ARO 23106.3-LS entitled "Protein-Modified Electrochemically Active Biomaterial Surface", dated Dec. 1988.

Samuels et al., "An Electrode-Support Oxidation Catalyst Based on Ruthenium (IV). pH 'Encapsulation' in a Polymer Film," *J. Am. Chem. Soc.*, vol. 103, pp. 307–312 (1981).

Denisevich et al., "Unidirectional Current Flow and Charge State Trapping at Redox Polymer Interfaces on Bilayer Electrode: Principles, Experimental Demonstration, and Theory," *J. Am. Chem. Soc.*, vol. 103, pp. 4727–4737 (1981).

Abruna et al., "Rectifying interfaces Using Two-Layer Films of Electrochemically Polymerized Vinylpridine and vinylbipyridine Complexes of Ruthenium and Iron on Electrodes," *J. Am. Chem. Soc.*, vol. 103, pp. 1–5 (1981).

Ellis et al., "Selectivity and Directed Charge Transfer Through an Electroactive Metallopolymer Film," *J. Am. Chem. Soc.*, vol. 103, pp. 7480–7483 (1981).

Gregg et al., "Cross-linked Redox Gels Containing Glucose Oxidase for Amperometric Biosensor Applications", 1990, pp. 258–263.

Couglan, "Concepts and Approaches to the Understanding of Electron Transfer Processes in Enzymes Containing Multiple Redox Centers", 1980, Chapter 5, *Molybdenum-Containing Enzymes*, pp. 187–220.

Nagy et al., "A New Type of Enzyme Electrode: The Ascorbic Acid Eliminator Electrode", *Life Sciences*, vol. 31, pp. 2611–2616, Pergamon Press, 1982.

Heller, A., "Electrical Wiring of Redox Enzymes", Reprinted from *Accounts of Chemical Research*, vol. 23, No. 5, 1990 (pp. 128–134).

Japanese Patent No. 03028752 A2 to Omochi et al., "Method for Manufacture of an Electrode Containing Immobilized Enzyme and Interfering-Substance— Eliminating Membrane," (Abstract), *Chemical Abstracts*, 114(21):203143u.

German patent No. 3934299 C1, "Enzyme Electrodes Containing Oxidase and Peroxidase" to Schmid et al., (Abstract), *Chemical Abstracts*, 114(23)225208w.

Japanese Patent Application No. 02310457 A2, "Enzyme Biosensor for Micro Analysis of Body Fluid" (Abstract), *Chemical Abstracts*, 114(21):203111a.

○ PHOSPHATE BUFFER
◇ SERUM

ENZYME ELECTRODES

This is a division of application Ser. No. 07/880,760 filed May 8, 1992 which is a continuation-in-part of copending application U.S. Ser. No. 389,226, filed Aug. 2, 1989.

FIELD OF THE INVENTION

This invention relates to amperometric biosensing electrodes for the detection of a specific analyte in a test sample. More particularly, this invention relates to novel biosensors containing a polymeric overcoating which confers increased sensitivity to the electrodes when used in biological fluids.

BACKGROUND OF THE INVENTION

Amperometric biosensors are capable of quantifying trace amounts of biological analytes such as glucose, urea, cholesterol, and the like in biological fluids. Analyte may be electroxidized directly at the electrode, or an enzyme may be immobilized on an electrode such that the reaction product of the enzyme with its substrate is detected by an electrical change, e.g., change in current flow, at the electrode. The current generated at the electrode is a function of the quantity of analyte in a sample.

Historically, electrical communication between enzyme and electrode has been achieved through the use of diffusing mediators. These include small diffusing redox shuttles such as ferrocenes, quinones, ruthenium amines, and the like. Enzyme electrodes using such mediators generally require that the enzyme and mediator shuttle be confined to the proximity of the electrode surface. The small shuttle molecules commonly employed can, however, readily diffuse through membranes that contain the enzyme. These membranes must allow passage of the enzyme's substrate, e.g., glucose and product e.g., gluconate or gluconolactone. Diffusion of the mediators away from the electrode surface results in reduced sensitivity of the electrode.

The inventors have previously reported the production of novel amperometric biosensors having a three-dimensional redox polymer network to which a redox enzyme is chemically bound. The three-dimensional redox molecular structure provides electrical contact between the surface of the electrode and the redox enzyme. Such electrodes are described in co-pending application U.S. Ser. No. 389,226 which is hereby incorporated by reference as if fully set forth and in Gregg and Heller, *J. Phys. Chem.*, 95:5970–5980 (1990) and Heller, *Accounts of Chem. Res.*, 23:128 (1990).

The three-dimensional redox network of these electrodes is preferably formed of a redox enzyme, a cross-linking agent, and a cross-linkable compound capable of reacting with the cross-linking agent and the redox enzyme. Either the cross-linkable compound or the cross-linking agent, or both, have multiple redox centers. When the compounds of each embodiment are mixed together under appropriate conditions, a chemical reaction takes place resulting in the formation of a cross-linked, three dimensional, redox polymer with the redox enzymes chemically bound within the cross-linked redox polymer network.

Materials known to produce the three-dimensional redox polymer network and effect the directly wired enzyme electrodes described above are limited. It would be desirable to have provided a variety of materials from which such electrodes could be produced and/or improved.

It has recently been found that the sensitivity of the three-dimensional redox polymer network electrodes described above in biological fluids such as serum or blood is decreased by a factor of 10–100 within 10 seconds as compared with sensitivity in a buffer solution. After loss of sensitivity in such a biological sample, the original sensitivity is recovered if the electrode is rinsed and retested in buffer.

It would be highly desirable to prevent this reversible loss of sensitivity of the three-dimensional redox polymer network enzyme electrodes to obtain an improved enzyme electrodes having high sensitivity.

SUMMARY OF THE INVENTION

The present invention includes novel redox polymers for the production of three-dimensional redox polymer networks for use in amperometric biosensors. The present invention also describes prevention of the reversible loss of sensitivity of three-dimensional redox polymer network enzyme electrodes in biological fluid such as blood and serum by the addition of a barrier to protein diffusion into the electrode, e.g., a thin polymeic film. The polymeric film prevents in-diffusion of proteins, particularly small proteins like albumin, yet allows continued good in-diffusion of redox enzyme substrate and good out-diffusion of reaction products, thereby preventing reduction in current output associated with diffusion of protein in the sample (e.g., albumin) to the 3-dimensional redox network.

DESCRIPTION OF THE FIGURES

FIG. is a schematic diagram of an electrode of the present invention.

DETAILED DESCRIPTION OF THE PREFERRED EMBODIMENT

Figure 1:
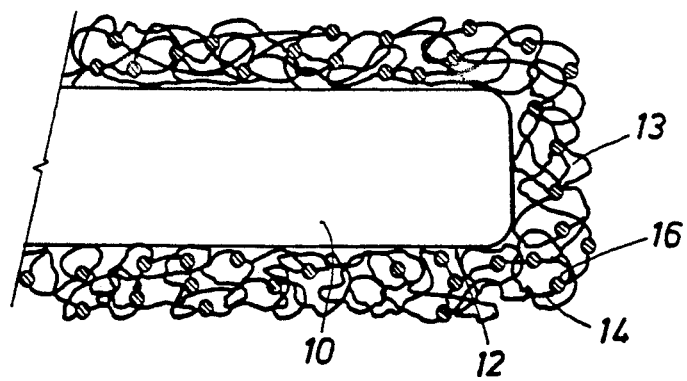

As shown in FIG. 1, a biosensor of the present invention includes an electrode 10 having a test surface 12. The surface 12 is substantially covered with a threedimensional redox polymer 14 to which is bound a redox enzyme 16. The three-dimensional redox polymer network 13 thus formed electrically connects the electrode 10 to a redox enzyme 16.

the electrode 10 may be formed of any material known for the manufacture of biosensing electrodes. Preferably the electrode is formed of a solid material, e.g., glassy carbon. Additional suitable electrode materials include graphite, platinum, palladium, tin oxide, and conducting organic salts.

The three-dimensional redox polymer includes at least two components which can combine to form a three-dimensional molecular structure. At least one of these components comprises a redox compound, and at least one other component comprises a redox enzyme. The resulting three-dimensional molecular structure has multiple redox centers and has the redox enzyme chemically bound within.

The term "bound within" describes a redox enzyme which is chemically, and preferably covalently, bonded to the redox polymer.

The redox enzyme may be glucose oxidase, D- or L-amino acide oxidase, lactate oxidase, and the like. It has now been found that cholesterol oxidase and theophylline oxidase are useful enzymes in the present invention.

The term "redox compound" is used herein to mean a compound that can be oxidized and reduced. The redox compound may have one or more functions that are reducible and oxidizable. Further, the term "redox compound" means a compound which contains one or more redox centers, "redox center" meaning a chemical function that accepts and transfers electrons.

The redox compounds, or recox centers contained within compounds useful in this invention may be organic or inorganic. Transition metal complexes with organic ligands such as bipyridine are preferred as redox centers because of their chemical stability and various oxidation states and their fast electron transfer kinetics. Examples of such complexes include polypyridine complexes of di- or trivalent osmium ions. Organic redox centers may also be employed, e.g., various derivatives of viologen (N,N'-bis alkyl-4,4'-bipyridine). A number of preferred crosslinkable compounds containing redox active centers are known. Some of these compounds require only the addition of enzymes to form 3-dimensional crosslinked films, i.e., the enzyme is the only required crosslinking agents. Other compounds do not directly react with chemical functions present on the enzyme and thus require a separate crosslinking agent to form the 3-dimensional network.

Figure 2:
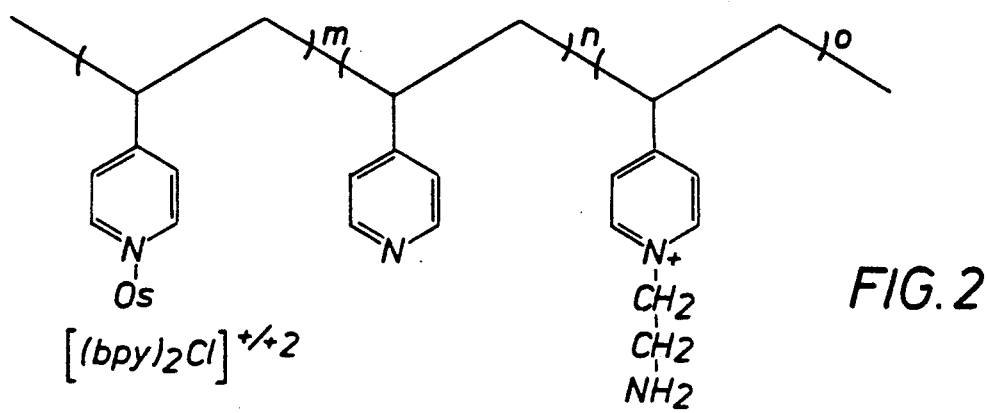
FIG. 2 is a diagrammatic representation of the structure of Polymer I (PVP-Os-NH$_2$).

A preferred redox polymer complex for use in the present invention is Polymer I, poly(vinylpyridine) complexed with [osmium bis (2,2'-bipyridine)Cl] (PVP-Os) which may be quaternized, e.g., with bromoethylamine to form a highly hydrophilic crosslinkable redox polymer containing pendant ethylamine groups (PVP-Os-NH$_2$) as shown in FIG. 2. Novel redox polymers useful in this invention also include derivatives of poly(N-vinyl imidazole) (PVI) complexed with [Os(-bpy)$_2$Cl]$^{+/2+}$ (PVI-Os) (Polymer II), shown, for example, in FIG. 3. PVI-Os (Polymer II), shown, for example, in FIG. 3. PVI-Os is a crosslinkable redox polymer, but may also be quaternized to form PVI-Os-NH$_2$ (Polymer III, shown in FIG. 4) for additional crosslinking sites.

In a preferred embodiment, the three-dimensional redox polymer network includes a redox enzyme, a cross-linking agent, and a cross-linkable compound capable of reacting with the cross-linking agent and the redox enzyme. Either the cross-linkable compound or the cross-linking agent, or both, contain multiple redox centers.

Preferred cross-linking agents are water soluble compounds that react under conditions where most enzymes are stable, that is, in water, between pH3 and pH9 at 0°–50° C. Included in this category of cross-linking agents are multi-functional epoxides such as polyethylene glycol diglycidyl ether (PEGDGE), carbodiimides, di- and poly- aldehydes, imidoesters, and N-hydroxysuccinimid esters. A number of reagents with limited solubility in water may also be used by dissolving them in a water-miscible organic solvent such as acetone, methanol, acetonitrile or dimethlformamide. Included in this category are reagents such as cyanuric chloride, tetrachlorobenzoquinone, and tetracyanoquinodimethane. These reagents may react with one or more types of functions including amines, alcohols, thiols and carboxylic acids which may be present on the surface of enzymes and which may also be included in the structure of the redox compound.

Additional crosslinkers which have now been found to be useful in the preparation of biosensors include di-, tri-, and poly-aziridines, e.g., pentaerythritol-tris-(B-(N-aziridinyl) propionate,

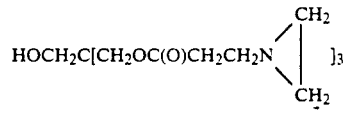

Preferred crosslinkable compounds are hydrophilic, containing chemical groups such as alcohols, carboxylic acids, amines, sulfonates, sulfates, phosphates, and phosphonates. Such groups tend to promote the solubility of the components in water which facilitates contact with the water soluble enzymes. Such groups may also improve the stability of the immobilized enzyme against denaturation.

To form the inventive electrodes, the components of the three-dimensional redox polymer network are mixed together under appropriate conditions such that a chemical reaction takes place resulting in the formation of a three-dimensional redox polymer having redox enzyme bound within a three-dimensional redox polymer network.

Mixture of redox enzyme and the various polymer components in a common solution is followed by the application of the solution to an electrode surface. Various application methods may be used, including the addition of drops of the solution onto the electrode surface, dip coating, spin coating, or spraying the solution onto the electrode surface. The application step is followed b.y a curing step such as drying in air or vacuum. Alternatively, the process may involve the addition of the enzyme and polymer components in separate solutions to the surface of the electrode, mixing, and then curing in air in an inert atmosphere or under vacuum.

Figure 5:
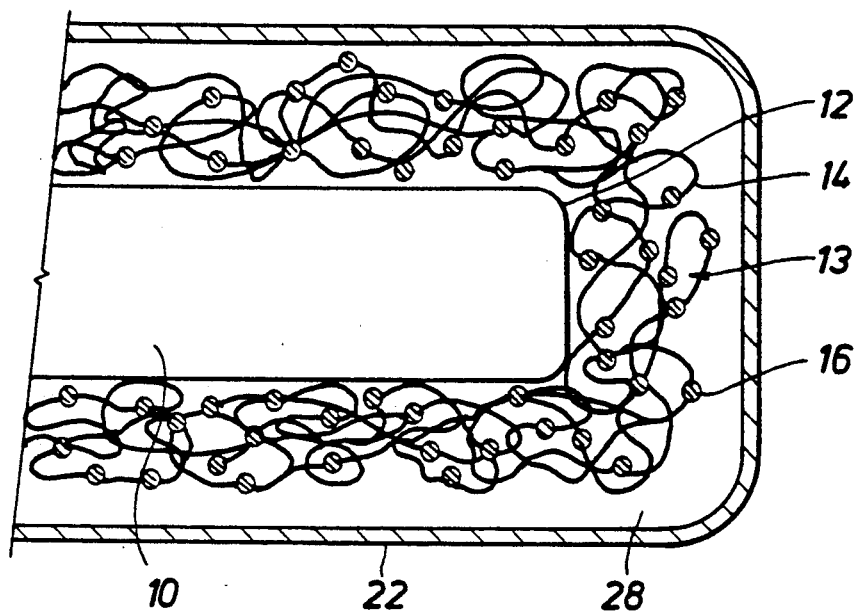
FIG. 5 is a diagrammatic representation of the coated enzyme electrodes of the present invention.

In a preferred embodiment, as shown in FIG. 5, the improved enzyme electrode of the present invention also includes a polymeric film 22 which prevents in diffusion of macromolecules, generally of molecular weights greater than 5000, such as serum albumin, from the assayed solution. The polymeric film 22 is preferably as thin as is practically feasible, subject to its having a low density of holes. The polymeric film 22 must be permeable to the substrate of redox enzyme 16 to allow good substrate in-diffusion and also permit good out-diffusion of product of the redox enzyme catalyzed reaction, i.e., gluconolactone or gluconate for a glucose electrode.

The polymeric film 22 may be directly applied to the surface of the redox polymer network 13, e.g., in direct physical contact, or may be positioned at a distance from the surface of the network 13, creating a space 28 between the film and the network 13. The latter may be preferred, for example, where the electrode 10 is located within a probe, e.g., a trochanter, into which sample solution may enter through a relatively narrow port. In this case, the polymeric film may span the entry port and thereby exclude communication of proteins with the redox polymer network.

It is hypothesized that protein such as albumin present in a biological sample may compete for redox polymer segments of the three-dimensional redox network and competitively replace segments of redox enzyme in the enzyme polymer complexes, may adversely interact with the enzyme, or both. The enzyme may remain covalently bound to the network even if some of the redox-network complex segments are competitively displaced by competing protein. Such complexing may reduce the fraction of electrons transported from the enzyme to the redox polymer network and thereby reduce the current generated at a given substrate concentration.

A polymeric film, through which the redox enzyme substrate and its generated products freely diffuse, but competing proteins such as albumin do not diffuse will be useful in the present invention. The preferred films are polyanionic, i.e. have at pH7 multiple bound anions, as polyanionic membranes exclude electrooxidizable anionic interferants. The inventive membranes exclude proteins and preferably exclude both proteins and electrooxidizable anions like urate and ascorbate. Examples of useful films include polycarbonate and polyurethane films. Especially preferred is Nafion, a commercially available, chemically-inert, polyanionic hydrophilic polymer. Most preferably, an electrode of the present invention effectively prevents undesired protein interactions with the enzyme/redox polymer layer, and also effectively eliminates small molecule interferants, as discussed in co-pending patent application U.S. Ser. No. 753,812 filed Sep. 3, 1991, which is hereby incorporated by reference as if fully set forth. The inclusion of a peroxidase or peroxidase-like catalyst reduces the number of interfering substances recognized at the electrode. Alternatively, anionic sites provided in the preferred protective films such as Nafion or palmitic acid-containing polyurethane films effectively exclude anionic interferants while the films prevent protein interactions with the redox polymer network.

Anionic sites may be included in the polymeric protective films. For example, multiple anionic functions may be provided in films containing carboxylate, sulfonate, phosphate, or phosphonate functions covalently bound to the polymer. In a preferred embodiment, the polymeric film contains fluorine.

In the method of the present invention, the inventive enzyme electrode is immersed into a test solution containing analyte, e.g., glucose. The analyte diffuses into the 3-dimensional redox polymer network where it may react with the redox enzyme, e.g., glucose oxidase, forming the reduced form of the enzyme and oxidized form of the analyte (e.g., gluconolactone). The reduced redox enzyme may then be oxidized by the redox centers of the redox polymer, e.g., the osmium complex. Electrons are subsequently transferred through the polymer to the electrode and the electrical current increases linearly with the concentration of the substrate over a substrate concentration range.

In the preferred, polymer-coated enzyme electrode of the present invention, the analyte (e.g., glucose) must readily diffuse through the polymeric coating to reach the redox enzyme. Also, the reaction product generated (e.g., gluconolactone or gluconate) must freely diffuse through the polymeric coating for quick removal. Interfering proteins present in biological fluids, e.g., albumin are prevented from contacting the redox polymer by the protective polymeric coating. In the most preferred embodiment, the polymer-coated enzyme electrode also contains a means to exclude anionic interferants, e.g., as discussed above.

EXAMPLES

The following examples are designed to illustrate certain aspects of the present invention. The examples are not intended to be comprehensive of all features and all embodiments of the present invention, and should not be construed as limiting the claims presented herein.

EXAMPLE 1

Aziridine Crosslinker

Electrodes where one enzyme of the group D-amino acid oxidase, L-amino acid oxidase, glycollate oxidase, cholesterol oxidase, theophylline oxidase, sarcosine oxidase, or galactose oxidase, was electrically connected through a 3-dimensional redox polymer network to an electrode were prepared as follows: First, poly(vinyl pyridine) was complexed with $[Os(bpy)_2Cl]^{+/2+}$ and then partly quaternized with ethylamine as described in copending U.S. Pat. application Ser. No. 389,226, to form Polymer I, PVP-Os-$NH_2$ as shown in FIG. 2. The resulting macromolecule was then complexed with one of the enzymes. The enzyme-polymer complexes were next crosslinked using hydroxylated triaziridine

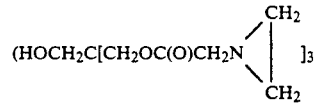

(PAZ) or poly(ethylene glycol) diglycidyl ether (PEGDGE). The ratio of enzyme to polymer was 0.57± 0.1 by weight. The ratio was adjusted to keep the total enzymatic activity on each of the different enzyme electrodes at approximately 0.01 units/electrode. The cross-linker containing enzyme-polymer complex solution was next deposited dropwise onto a polished vitreous carbon disk electrode. The electrode was cured for approximately 24 hours in a vacuum desiccator at 22° C. The cured electrode was then extensively washed in pH 7.2 phosphate buffer, while rotated at 1000 rpm, for 3-5 hours. The thickness of the resulting films (when wet) was 1-2μm.

The prepared electrodes were used in a test solution of 30mM phosphate buffer (pH 7.2) with 0.15M NaCl, except in the case of cholesterol oxidase, where this buffer was diluted with an equal volume of isopropanol and contained 0.5% Triton X-100. The electrodes were poised at 0.45V (SCE). After a steady base line was reached a substrate solution was injected. The substrates included D-alanine for D-amino acid oxidase; L-leucine for L-amino acid oxidase; glucose for glucose oxidase; cholesterol for cholesterol oxidase, etc. In the case of theophylline oxidase, theophylline addition made the test solution more acidic. The electrodes were rotated during the assay at 1000 rpm.

Table I lists the characteristics of some of these prepared electrodes when each was used to measure its specific substrate, including the current density, apparent Km, and sensitivity. Each data point is the mean of four electrode measurements.

TABLE I

| Enzyme | Crosslinker | Electrode Km (mM) | Highest Current Density ($\mu Acm^{-2}$) | Sensitivity* ($AM^{-1} cm^{-2}$) |
| --- | --- | --- | --- | --- |
| D-AMINO ACID OXIDASE | PAZ | 1.000 | 20.0 | 0.0100 |
| THEOPHYLLINE OXIDASE | PAZ | 0.047 | 2.9 | 0.0310 |
| GLYCOLLATE OXIDASE | PEGDGE | 0.900 | 17.0 | 0.0090 |
| CHOLESTEROL OXIDASE | PEGDGE | 0.250 | 2.3 | 0.0048 |
| GALACTOSE OXIDASE | PEGDGE | 30.000 | 100.0 | 0.0030 |

*at the substrate concentration corresponding to the apparent Km.

Figure 6:
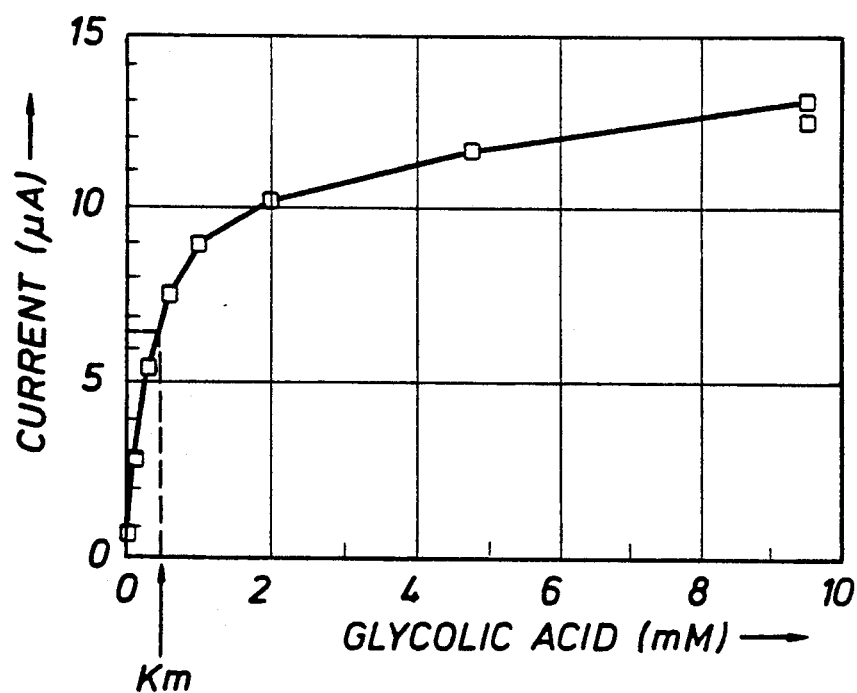
FIG. 6 is a graphical representation of current generated in response to glycollate by a glycollate electrode formed with a PAZ triaziridine-type crosslinker.
Figure 7:
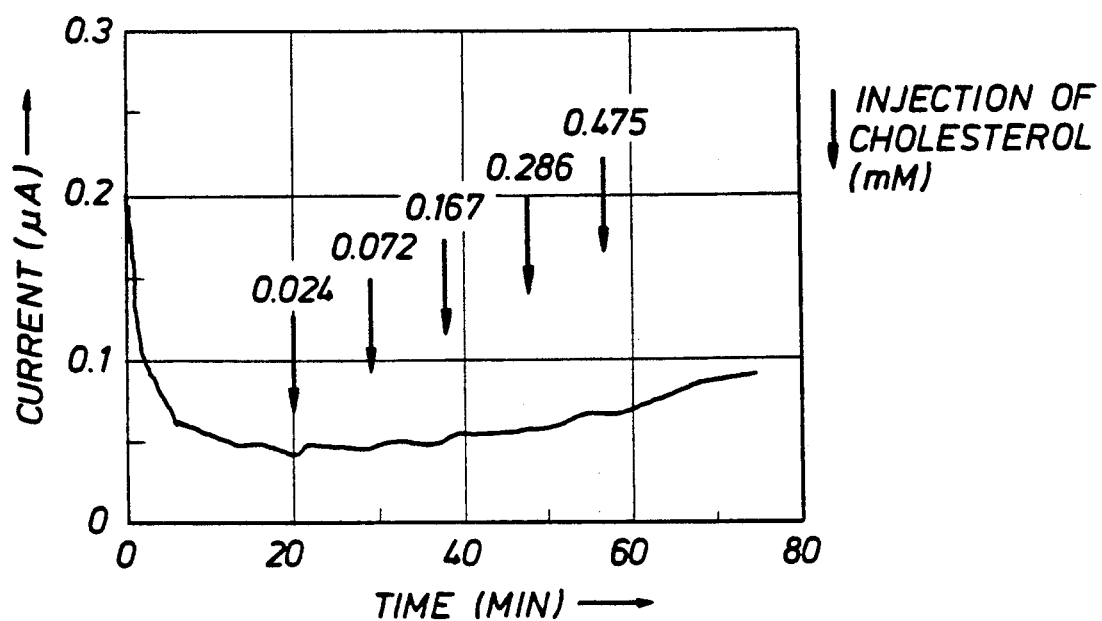
FIG. 7 is a graphical representation of current generated in response to cholesterol by a cholesterol oxidase electrode of the present invention.

The steady state current response of the glycollate oxidase-containing electrode to varying concentrations of glycollate is shown in FIG. 6; FIG. 7 shows the steady state current response of the cholesterol oxidaze-containing electrode when cholesterol (in isopropanol) was injected so as to bring the total cholesterol concentration to the indicated level. e.g., 0.024–0475mM. FIGS. 6 and 7 show that the currents increase with substrate concentration over the concentration ranges shown.

EXAMPLE 2

Preparation of PVI-Os

Vinyl imidazole was mixed with water at a ratio of 2:1 (by weight) and the resulting 7M solution was purged with argon for 15 minutes. The container was then sealed and δ-irradiated by a radioactive cobalt source (Co-60) with 2.5MRad at a rate of 100kRad/hour. The resulting polymer was then precipitated by adding the irradiated solution to 4L of a mixture of 1:2 acetone:hexane. The precipitated polymer was redissolved in MeOH and again reprecipitated from 1:2 acetone:hexane. The poly(vinyl imidazole) (PVI) was then dried in a vacuum at 90° C.

Figure 3:
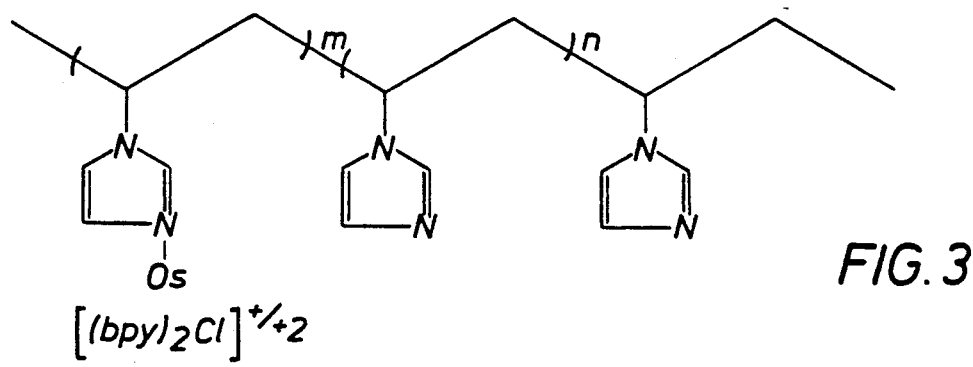
FIG. 3 is a diagrammatic representation of the structure of Polymer II (PVI-Os).
Figure 4:
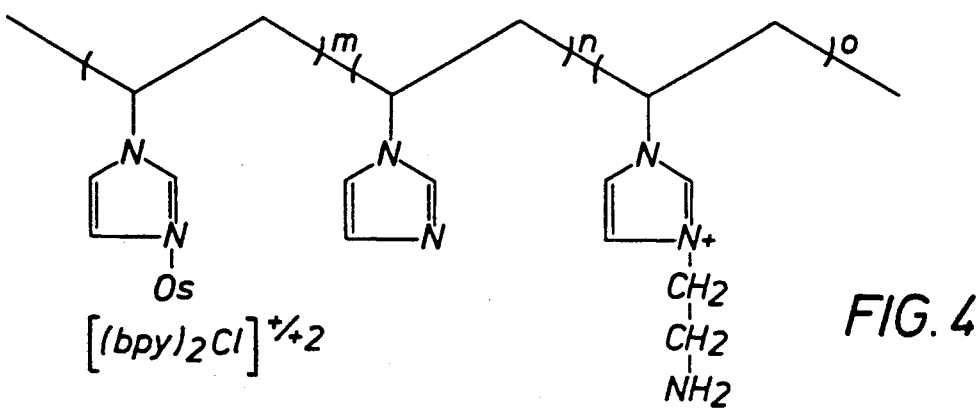
FIG. 4 is a diagrammatic representation of the structure of Polymer III (PVI-Os-NH$_2$).

The PVI (1.92 grams) was next further purified by dissolving in 30mL MeOH and precipitating with ether (2L). This dissolution-precipitation was repeated for a total of three times. The precipitated PVI weighing 380mg, and 456mg of $Os(2,2'$-bis bipyridine$)_2Cl_2$ were dissolved in 100 ml EtOH. The solution was refluxed under nitrogen for five days. The resulting complex, PVI-Os, (Polymer II, as shown in FIG. 3) was precipitated by adding 2L ether and the precipitate dried in a vacuum at 38° C. for 2 hours. This procedure follows that described by Forster and Vos, *Macromolecules*, 23:4372–4377, 1990, except that more of the osmium complex was reacted with the PVI and the osmium complex content of the PVI-Os was correspondingly higher.

Unlike PVP-Os, PVI-Os itself may be cross-linked with an enzyme, using a crosslinking agent to form a 3-dimensional redox polymer network of the inventive electrodes. Alternatively, PVI-Os may be quaternized to form PVI-Os-NH$_2$ (Polymer III of FIG. 4) which contains additional crosslinkable ethylamine functions.

To form PVI-Os-NH$_2$, 600mg PVI-Os was added to 1.23g 2-bromoethylamine dissolved in 18 ml ethylene glycol and 30 ml dimethyl formamide. This mixture was reacted at 64° C. for 24 hours. The resulting polymer was then precipitated by adding the solution of PVI-Os-NH$_2$ to acetone (2L) and filtered. The polymer was redissolved in 30 ml H$_2$O and the bromide ions were exchanged with chloride using an anion exchange resin.

The beads were filtered after 24 hours, then 20 ml of H$_2$O was added to the filtered solution, which was dialyzed against water for 48 hours. A Spectrapor TM dialysis membrane having a molecular weight cutoff of 3500 was used for dialysis. The PVI-Os-NH$_2$ polymer was obtained upon vacuum evaporation of the water.

EXAMPLE 3

Glucose Electrodes Formed of PVI-Os and PVI-Os-NH$_2$

Glassy carbon 3 mm diameter electrodes were polished with sand paper (400 and 600 grit) and with alumina (20, 5, 1 and 0.3μm). A glucose electrode was prepared by the sequential addition of 1μl PVI-Os or 1μl PVI-Os-NH$_2$ polymer, 5mg/ml in H$_2$O; 1μl glucose oxidase (GOD), 5mg/ml in H$_2$O; and 1μl PEGDGE, 0.5mg/ml in H$_2$O, dropwise onto the electrode, with stirring. The electrode was permitted to cure in air at room temperature for 15 hours.

Figure 8:
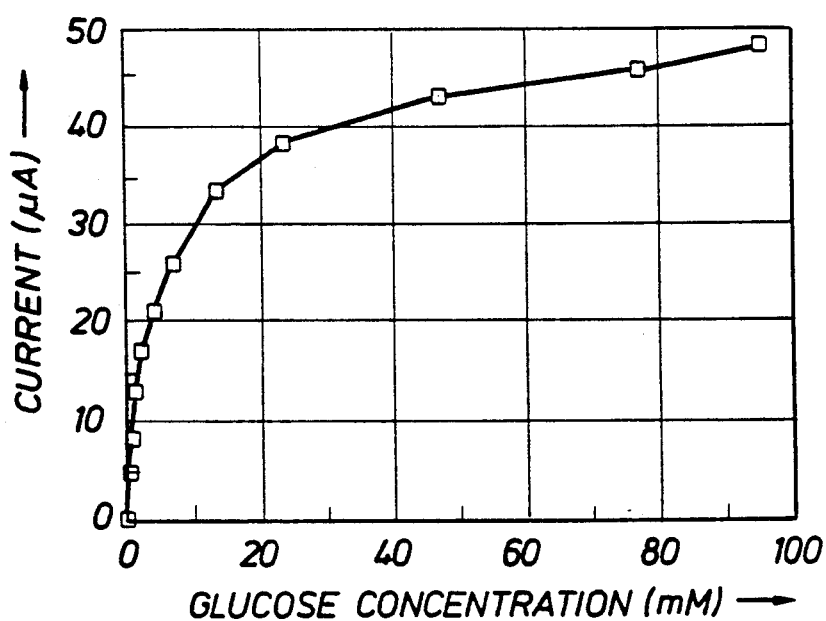
FIG. 8 is a graphical depiction of the current generated in response to glucose by a glucose electrode containing PVI-Os redox polymer.
Figure 9:
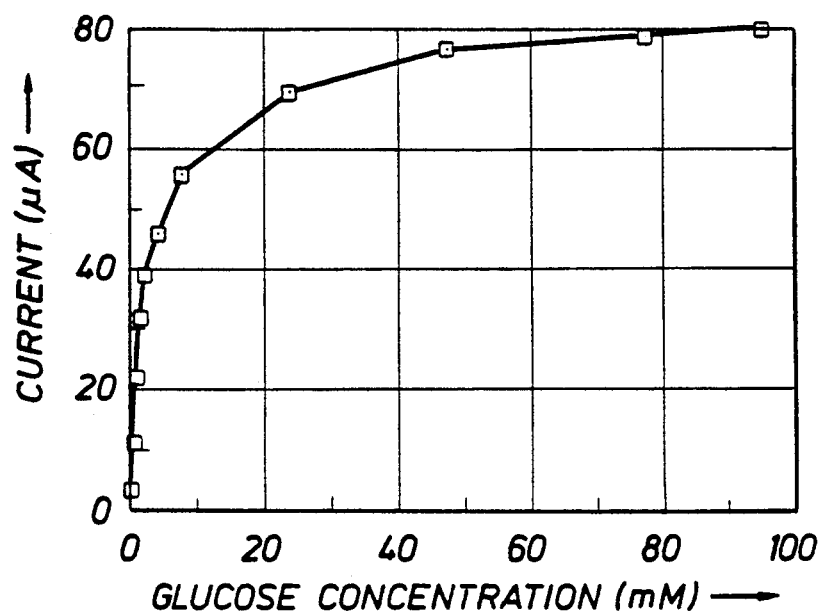
FIG. 9 is a graphical depiction of the current generated in response to glucose by a glucose enzyme electrode containing a PVI-Os-NH$_2$ redox polymer.

The glucose electrodes made with PVI-Os and PVI-Os-NH$_2$ polymers were tested in a test solution to which increasing amounts of glucose were added. These glucose calibration curves were obtained under argon at 21.3° C. and 1000 rpm electrode rotation. FIG. 8 shows the current generated in response to glucose from the glucose oxidase electrode prepared from the novel redox polymer PVI-Os. FIG. 9 shows the current generated in response to glucose from the glucose oxidase electrode prepared from the novel redox polymer PVI-Os-NH$_2$.

EXAMPLE 4

Preparation and Testing of 3-Dimensional Redox Polymer Enzyme Electrodes

Figure 10:
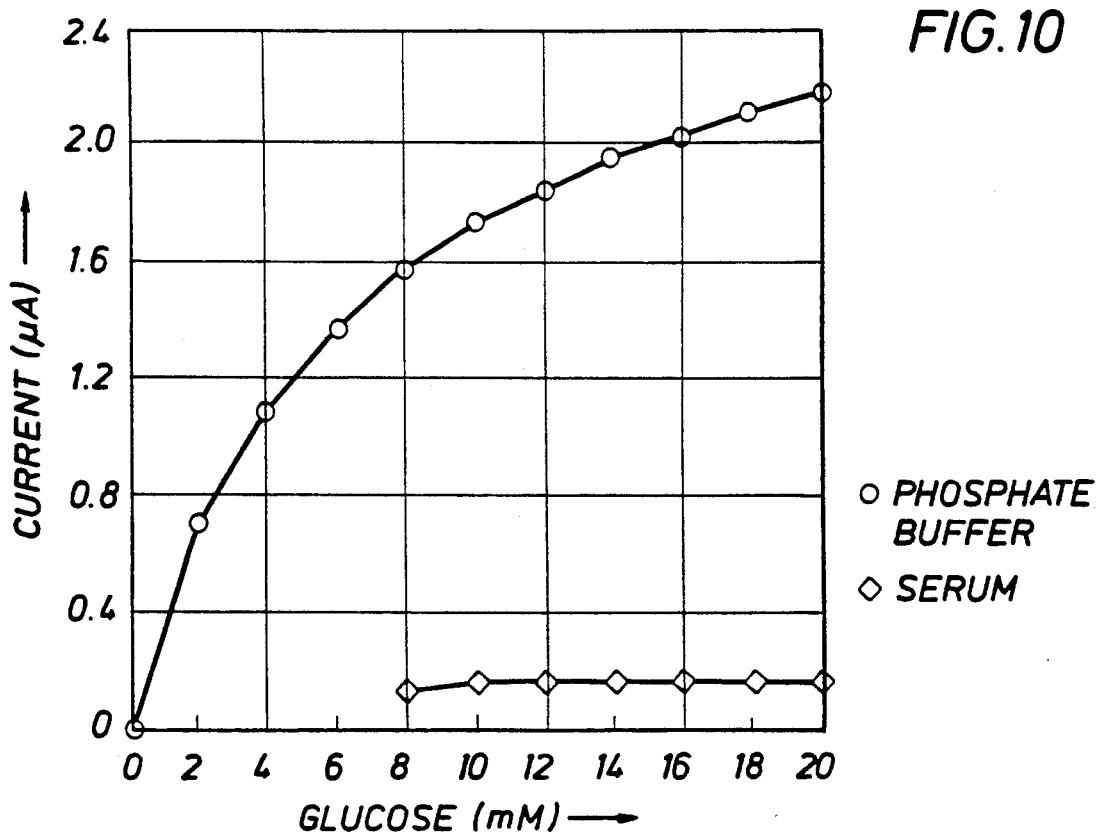
FIG. 10 is a graphical depiction of the current generated in response to glucose in buffer or serum by a glucose electrode (non-coated).

Three-dimensional redox polymer glucose electrodes were prepared and tested in the presence of glucose as described previously (see copending patent application U.S. Ser. No. 389,226; Gregg and Heller, *J. Phys. Chem*, 95:5970–5980, 1991; and Pishko et al., *Anal. Chem.*, 63:2268–2272, 1991). The electrodes were tested in the presence of glucose in phosphate buffer as compared with serum samples. The results as shown in FIG. 10 demonstrate a difference in the response of the glucose sensor in phosphate buffer as compared with serum. A decrease in sensitivity of the glucose electrode was seen in the serum sample as compared with the buffer sample. The loss of sensitivity of these electrodes in the serum sample was substantial.

EXAMPLE 5

Glucose Electrode Containing Polyurethane Overcoating

Figure 11:
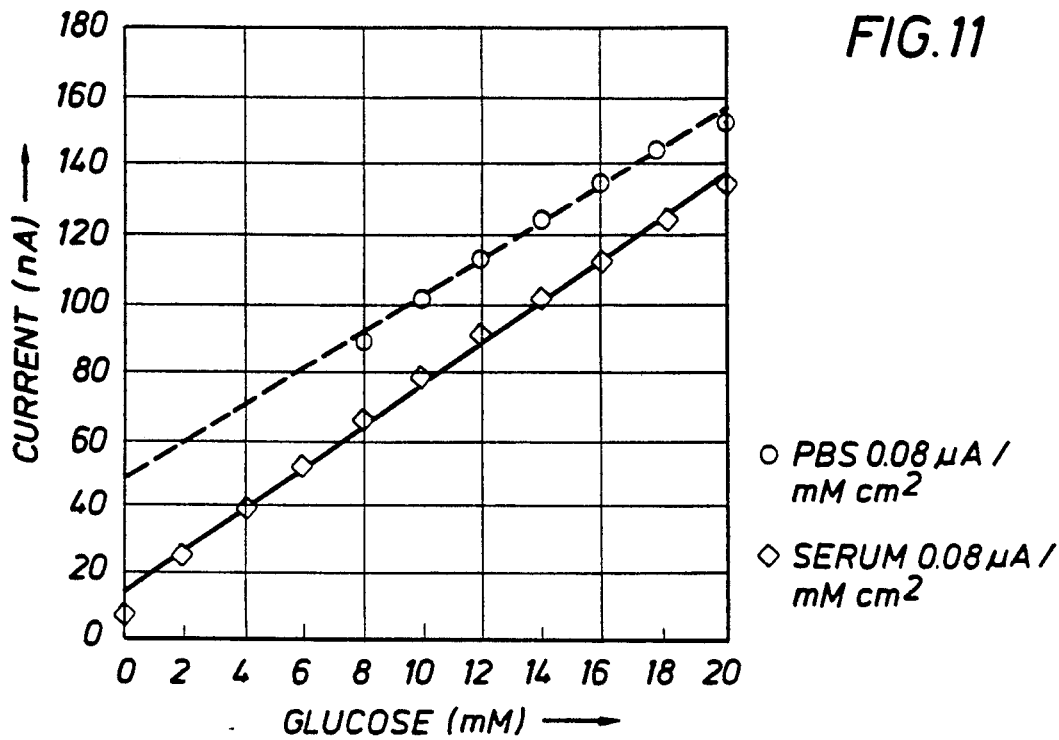
FIG. 11 is a graphical depiction of the current generated in response to glucose in buffer or serum by a glucose electrode which has been coated with polyurethane.

A three-dimensional redox polymer glucose electrode was prepared as described for Example 4. The prepared glucose electrode was then coated with a mixture of medical-grade polyurethane (PELLETHANE, Dow Chemical) and palmitic acid. The polyurethane served as a protein exclusion barrier and palmitic acid served to place negative charges within the polyurethane film to exclude ascorbate and urate. The polymeric film was applied to the electrodes' surface by dip coating The electrode in 2% polyurethane, 1% palmitic acid codissolved in tetrahydrofuran (THF). The polymeric film was allowed to solidify on the electrodes in humidified air for six hours, after which the film-coated electrodes were washed in phosphate buffered saline for two days so as to hydrate the polymeric film and remove any residual solvent.

the coated enzyme electrodes were then tested in glucose containing solutions prepared in either phosphate buffered saline (buffer) or in serum. The results, shown in FIG. 11, demonstrated no loss of sensitivity of the coated glucose electrode in the serum sample. The difference in glucose sensitivity was small (approximately 15%). The palmitate anions in the film were effective in excluding interfering ascorbate and urate anions from the steep increase in current seen in the absence of an interference eliminating layer (*J. Am. Chem. Soc.*, 113:9003–4, 1991). There was no such increase when physiological concentrations of urate or ascorbate were added.

EXAMPLE 6

Glucose Electrode Containing NAFION Overcoating

Figure 12:
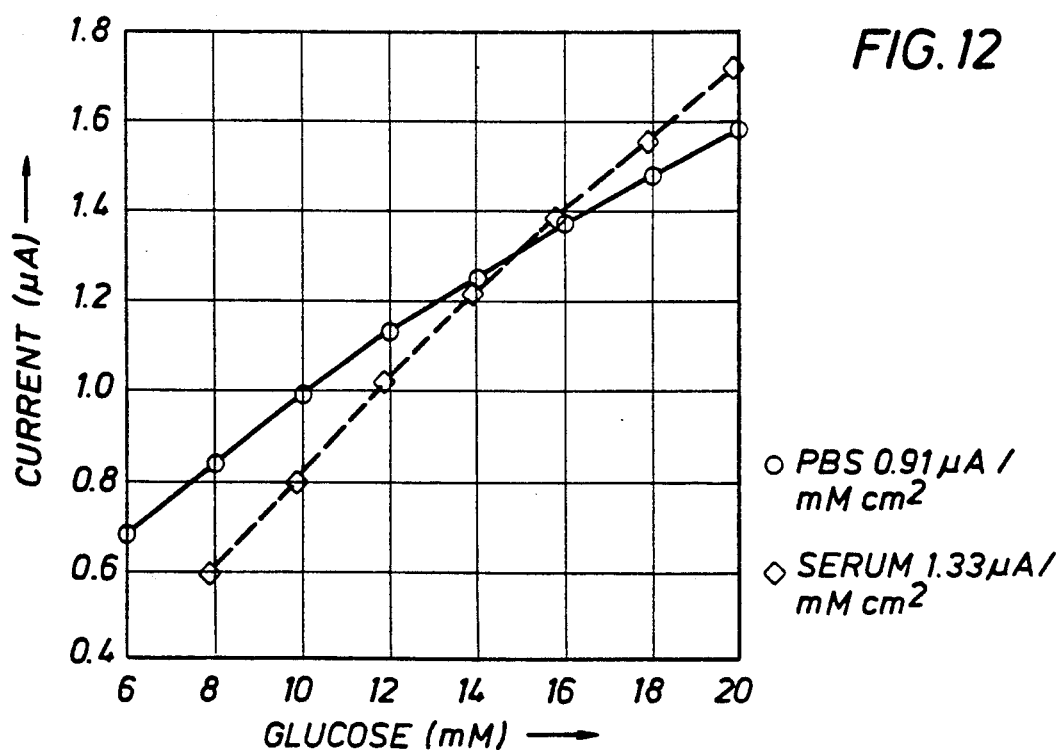
FIG. 12 is a graphical depiction of the current generated in response to glucose in buffer or serum by a glucose electrode which has been coated with Nafion.

A threedimensional redox polymer glucose electrode prepared as described for Example 4 was coated with a perfluorosulfonate ion exchange resin (NAFION TM, purchased from Aldrich Chemical Company). Nafion was applied to the glucose electrode surface by dipping the electrode into a solution of 0.5% Nafion in 90% ethanol, 10% $H_2O$. The ensuing droplet on the electrode surface was allowed to dry in air for approximately two hours. The electrode was then dip coated again, dried, and then soaked in phosphate buffered saline for two hours prior to use. The glucose concentration dependence of the current of the Nafion-coated electrode in serum as compared with buffer (PBS) is shown in FIG. 12. Only a minor difference between the two response curves was observed.

We claim:

1. An enzyme electrode comprising:
   an electrode having a testing surface;
   a transducing film covering the testing surface, which film comprises a cross-linked redox polymer network to which a redox enzyme is chemically bound, wherein the redox enzyme electrically communicates through the film with the electrode thereby transducing substrate flux to an electrical current; and
   a polymeric film covering the transducing film and excluding from the transducing film proteins of molecular weights exceeding 5000 daltons.

2. The enzyme electrode of claim 1, wherein the polymeric film is polyurethane.

3. The enzyme electrode of claim 2, wherein the polymeric film further includes palmitic acid.

4. The enzyme electrode of claim 1, wherein the polymeric film is polycarbonate.

5. The enzyme electrode of claim 1, wherein the polymeric film includes multiple anionic functions covalently bound to the polymeric film.

6. The enzyme electrode of claim 5, wherein the polymeric film includes multiple carboxylate, sulfonate, phosphate, or phosphonate functions covalently bound to the polymeric film.

7. The enzyme electrode of claim 6, wherein the polymeric film contains fluorine.

* * * * *